United States Patent [19]

Arai et al.

[11] 4,336,249
[45] Jun. 22, 1982

[54] ANTIBIOTIC SUBSTANCE

[75] Inventors: Mamoru Arai; Akio Torikata; Ryuzou Enokita; Tatsuo Haneishi; Mutsuo Nakajima, all of Hiromachi, Japan

[73] Assignee: Sankyo Company Limited, Tokyo, Japan

[21] Appl. No.: 41,501

[22] Filed: May 22, 1979

[30] Foreign Application Priority Data

May 24, 1978 [JP] Japan ................................ 53/62042

[51] Int. Cl.³ ............................................ A61K 35/00
[52] U.S. Cl. .................................... 424/121; 435/169
[58] Field of Search ......................... 424/121; 435/169

[56] References Cited

U.S. PATENT DOCUMENTS

| | | | |
|---|---|---|---|
| 3,365,362 | 1/1968 | Mancy et al. | 167/65 |
| 3,719,656 | 3/1973 | Jolles | 167/65 |
| 4,123,521 | 10/1978 | Hawka et al. | 424/121 |

Primary Examiner—Jerome D. Goldberg
Attorney, Agent, or Firm—Frishauf, Holtz, Goodman & Woodward

[57] ABSTRACT

A novel antibiotic substance, named "Mycoplanecin", of presently unknown structural formula, is produced by cultivating a Mycoplanecin-producing microorganism of the genus Actinoplanes, especially the *Actinoplanes nov.* sp. Strain No. 41042, NRRL No. 11462.

3 Claims, 3 Drawing Figures

FIG. I

ANTIBIOTIC SUBSTANCE

BACKGROUND AND SUMMARY OF THE INVENTION

The present invention relates to a novel antibiotic substance, named Mycoplanecin, to a novel microorganism, *Actinoplanes nov.* sp. Strain No. 41042 capable of producing Mycoplanecin, and to a process for producing Mycoplanecin by cultivating a Mycoplanecin-producing mciroorganism of the genus Actinoplanes.

The novel antibiotic substance, Mycoplanecin, can be characterized by the following physical and chemical properties:

1. Colour and state
   White powder.
2. Melting point
   161°–167° C.
3. Specific rotation
   $[\alpha]_D^{21}$-66° (C=0.4, chloroform).
4. Elemental anaylsis
   C, 61.78%; H, 8.48%; N, 11.75%. (After drying to constant weight)
5. Ultraviolet absorption spectrum
   Only terminal absorption as shown in FIG. 1 of the accompanying drawings, when measured at 20 μg/ml in a 50% v/v aqueous methanolic solution.
6. Infrared absorption spectrum
   The spectrum, measured in a KBr disc, is shown in FIG. 2 of the accompanying drawings.
7. Nuclear magnetic resonance spectrum
   The spectrum, as measured in deuterochloroform as solvent and with tetramethylsilane (TMS) as internal standard, is shown in FIG. 3 of the accompanying drawings.
8. Solubility
   Soluble in methanol, ethanol, ethyl acetate, acetone and chloroform.
   Sparingly soluble in benzene.
   Insoluble in water.
9. Colour reaction
   Brown-coloured with 50% v/v aqueous sulphuric acid. Positive for iodine and potassium permanganate on silica gel thin layer chromatograms. Negative for ninhydrin and 2,4-dinitrophenylhydrazine.
10. Amino acid composition
    1 mole each of glycine, proline, leucine, 2-amino-5-methylhexanoic acid, N-methylthreonine, N-methylleucine, methylpropline and ethylproline, and 2 moles of N-methylvaline detected after hydrolysis with 6 N hydrochloric acid at 105° C. for 20 hours.
11. Antibacterial activity
    Strong antibacterial activity against various bacteria of the genus Mycobacterium.

In addition, Mycoplanecin has Rf values (on silica gel thin layer chromatography, F254, 0.25 mm, No. 5715, available from Merck and Co. Inc) of 0.15 when developed with ethyl acetate and 0.64 when developed with a 95:5 by volume mixture of chloroform and methanol.

The novel microorganism of the invention is *Actinoplanes nov.* sp. Strain No. 41042, which was isolated from a sample of soil collected in Sumoto City, Hyogo Prefecture, Japan. The strain has been deposited under Accession No. FERM-4504 with the Technical Research Institute of the Microbial Industry, Agency of Industrial Science and Technology, Ministry of International Trade and Industry, Japan. The strain has also been deposited under Accession No. NRRL-11462 with the U.S. Department of Agriculture.

Also provided, as part of the present invention, is a method of producing the new antibiotic substance, Mycoplanecin, which comprises cultivating a Mycoplanecin-producing microorganism of the genus Actinoplanes and then isolating Mycoplanecin from the culture.

DETAILED DESCRIPTION OF INVENTION

Figure 1:
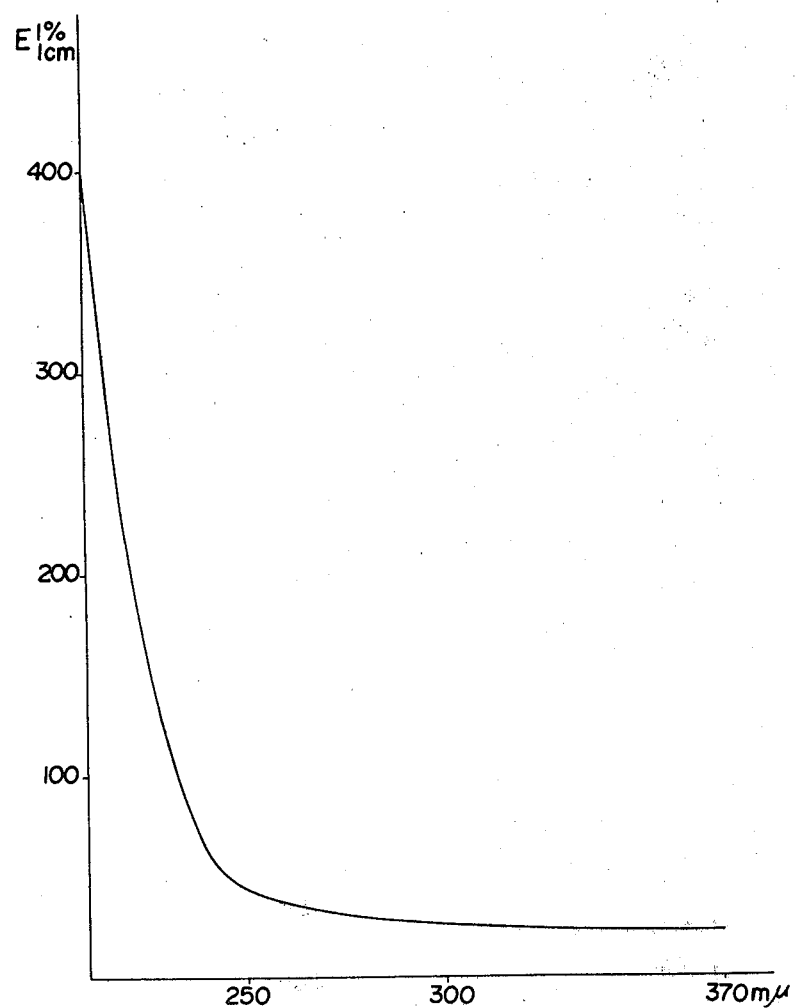

Morphological characteristics and physiological properties of *Actinoplanes nov.* sp. Strain No. 41042 are as described below:

1. Morphological characteristics

When cultivated on medium ISP4 prescribed by the International Streptomyces Project (ISP) at 28° C. for 14 days and observed under a microscope Strain No. 41042 exhibited the following morphological characteristics: spherical to subsperical sporangia with an ordinary diameter of 7–15 μ; and spores of size $0.8\mu \times 1.3\mu$, with flagella and having a motility in a 1/15 M phosphate buffer of pH 7.0 of about 40 minutes. The growth results on various media at 28° C. for 14 days are shown in Table 1.

TABLE 1

| Type of medium | Item | Characteristics of strain No. 41042 |
|---|---|---|
| Yeast . malt agar (ISP 2) | SM | Abundant, dark yellowish orange (8-7-8) |
|  | AM | Not grown |
|  | SP | Not produced |
|  | SG | Not formed |
| Oatmeal . agar (ISP 3) | SM | Abundant, yellowish brown (10-6-8) |
|  | AM | Trace aerial mycelia |
|  | SP | Pale yellowish brown (4-8-9) |
|  | SG | Not formed |
| Starch . salts agar (ISP 4) | SM | Moderate, dark yellowish orange (8-7-8) |
|  | AM | Not grown |
|  | SP | Not produced |
|  | SG | Abundant |
| Glycerol . asparagine agar (ISP 5) | SM | Abundant, pale yellowish brown (4-8-8) |
|  | AM | Not grown |
|  | SP | Not produced |
|  | SG | Not formed |
| Tyrosine-agar (ISP 7) | SM | Abundant, light brown (8-6-7) |
|  | AM | Not grown |
|  | SP | Pale yellowish brown |
|  | SG | Not formed |
| Nutrient agar | SM | Less good, pale orange (4-8-7) |
|  | AM | Not grown |
|  | SP | Not produced |
|  | SG | Not formed |
| Emerson's agar | SM | Moderate, pale yellowish brown (6-8-8) |
|  | AM | Not grown |
|  | SP | Yellowish brown (10-6-8) |
|  | SG | Not formed |
| Water agar | SM | Poor, yellowish gray (1-9-10) |
|  | AM | Not grown |
|  | SP | Not produced |
|  | SG | Moderately formed |
| Calcium malate agar | SM | Moderate, pale orange (4-8-7) |
|  | AM | Not grown |
|  | SP | Not produced |
|  | SG | Slightly formed |
| Hickey-Tresner's agar | SM | Abundant, yellowish brown (8-6-8) |

TABLE 1-continued

| Type of medium | Item | Characteristics of strain No. 41042 |
|---|---|---|
| | AM | Slight trace aerial mycelia grown |
| | SP | Not produced |
| | SG | Not formed |
| Bennett's agar | SM | Abundant, dark yellowish orange (8-7-8) |
| | AM | Not grown |
| | SP | Not produced |
| | SG | Slightly formed |
| Sucrose-nitrate agar | SM | Less good, pale orange (4-8-7) |
| | AM | Not grown |
| | SP | Not produced |
| | SG | Abundant |
| Glucose asparagine agar | SM | Moderate, brownish white (2-9-8) |
| | AM | Not grown |
| | SP | Not produced |
| | SG | Slightly formed |
| Tomato paste oatmeal agar | SM | Moderate, pale yellowish brown (6-8-9) |
| | AM | Not grown |
| | SP | Not produced |
| | SG | Not formed |
| Glycerol glycin agar | SM | Abundant, pale yellowish brown (6-8-8) |
| | AM | Not grown |
| | SP | Not produced |
| | SG | Not formed |
| Glucose nitrate agar | SM | Moderate, dark yellowish orange (8-7-8) |
| | AM | Not grown |
| | SP | Dark yellow (10-7-9) |
| | SG | Not formed |

Abbreviations:
SM: Substrate mycelium
AM: Aerial mycelium
SP: Soluble pigment
SG: Sporangium 2. Physiological characteristics The physiological characteristics of Strain No. 41042 are given in Table 2.

TABLE 2

| | |
|---|---|
| Tyrosinase reaction | Positive (strong) |
| Nitrate reduction | Positive (strong) |
| Hydrolysis of starch | Negative |
| Gelatin liquefaction | Positive (strong) |
| Peptonization of milk 26° C. | Positive (pH 6.0) |
| Coagulation of milk 26° C. | Positive |
| Melanin formation: | |
| Medium A | Positive |
| Medium B | Positive |
| Temperature range for growth (on ISP 2 medium) | 9.0–32.5° C. (Optimum temperature for growth 18.5–29° C. |

The media used were as follows:
Medium A: Tryptone-yeast extract broth (ISP 1).
Medium B: Peptone-yeast extract-iron agar (ISP 6).

The carbon source utilization pattern of Strain No. 41042 on Pridham-Gottlieb's agar medium at 28° C. after 14 days is shown in Table 3.

TABLE 3

| Medium | C | D | Medium | C | D |
|---|---|---|---|---|---|
| D-Glucose | ++ | ++ | Raffinose | − | − |
| L-Arabinose | ++ | ++ | Inulin | − | − |
| D-Xylose | ++ | ++ | Dextrin | ++ | ++ |
| D-Fructose | + | ++ | Starch | + | + |
| L-Rhamnose | + | ++ | i-Inositol | − | − |
| D-Galactose | ++ | ++ | D-Mannitol | − | + |
| D-Mannose | ++ | ++ | Dulcitol | − | − |
| Sucrose | + | ++ | Salicin | − | − |
| D-Cellobiose | + | ++ | Sodium acetate | − | − |
| Melibiose | − | − | Sodium succinate | − | − |
| β-Lactose | − | + | Glycerol | − | ++ |
| Maltose | + | + | Cellulose | − | − |
| Trehalose | − | + | Control | − | − |

++: Well utilized
+: Utilized
−: Not utilized

The following media were used:
Medium C: Pridham-Gottlieb's agar.
Medium D: Pridham-Gottlieb's agar plus yeast extract 0.5%.

3. Mycelium components

An acid hydrolyzate of the mycelia was analyzed by paper chromatography according to the methods described by B. Becker et al in Applied Microbiology, 12, 421–423 (1964) and 13, 236—243 (1965) and by M. P. Lechevalier et al in "The Actinomycetales" by H. Prauser, 311–316 (1970). The results are shown in Tables 4 and 5.

TABLE 4

| Cell wall type | | | | | |
|---|---|---|---|---|---|
| Type of diaminopimelic acid | | | Glycine | Arabinose | Galactose |
| Meso | LL | Hydroxy | | | |
| + | − | + | + | Trace | + |

From these results, it is confirmed that the cell wall type is II.

TABLE 5

| Saccharide components in whole cell | | | | |
|---|---|---|---|---|
| Glucose | Galactose | Mannose | Arabinose | Xylose |
| + | + | Trace | Trace | Trace |

As can clearly be seen from the properties described above, Strain No. 41042 belongs to the genus Actinoplanes of the family Actinoplanaceae, within the group of actinomycetes. This conclusion is based upon the formation of spherical to subspherical sporangia, motile spores and cell walls of type II; the new strain is therefore named Actinoplanes nov. sp. Strain No. 41042.

As is well-known, the properties of actinomycetes, including Actinoplanes, strains are not fixed and they readily undergo mutation both though natural causes and as the result of artificial mutation. Although the invention relates to the production of the new antibiotic Mycoplanecin especially by the cultivation of the above-defined Actinoplanes nov. sp. Strain No. 41042, it also includes within its scope the use of mutants of this organism and generally of any Actinoplanes strain which is capable of producing Mycoplanecin, in order to obtain this antibiotic substance.

The cultivation of the Mycoplanecin-producing microorganism, in accordance with the process of the invention, can be performed under the conditions conventionally employed for the cultivation of Actinoplanes species. Shaken culture or submerged culture with aeration and agitation in a liquid medium are preferred.

The nutrient medium used for the cultivation can be of a composition such as is conventionally used for the cultivation of actinomycetes. Thus, it contains: an assimilable carbon source, e.g. glucose, arabinose, galactose, mannose, sucrose, maltose, dextrin, starch, glycerin, a vegetable fat or oil (such as soybean oil, corn oil or cottonseed oil), an animal fat or oil (such as chicken oil or lard) or fish oil; an assimilable nitrogen source, e.g. soybean meal, peanut oil, cottonseed meal, fish meal, corn steep liquor, oatmeal, skimmed milk, peptone, meat extract, live yeast, yeast extract, casamino acid, sodium nitrate, ammonium nitrate or ammonium sulphate; and an inorganic salt, e.g. sodium chloride, potassium chloride, phosphates, magnesium carbonate, calcium carbonate or calcium chloride. It may also contain minor amounts of various other metal salts, for example ferrous sulphate, copper sulphate, magnesium sulphate, zinc sulphate or cobalt sulphate.

Cultivation in a liquid medium is preferably performed aerobically, with aeration and agitation, in which case an anti-foaming agent may be added to the medium; suitable anti-foaming agents include silicone oils, vegetable oils or surfactants.

The cultivation is suitably performed at a substantially neutral pH value and at a temperature of from 18° to 30° C., preferably about 28° C.

The titre of Mycoplanecin produced in the culture broth as cultivation proceeds can be quantitatively determined by the cup assay method using *Mycobacterium smegmatis* ATCC 607 as the test microbe. The maximum production of Mycoplanecin is generally achieved after 3-5 days of cultivation.

Mycoplanecin is present in both the liquid portion and the mycelial portion of the culture broth produced by the process of the invention. In order to recover the antibiotic from the culture broth on completion of the cultivation, the mycelium and other solids are first removed from the liquid phase by filtration, for example using diatomaceous earth as a filter aid, or by centrifugation. The Mycoplanecin which is present in the mycelial portion or the filtrate or the supernatant can then be isolated and purified by conventional techniques suited to its physico-chemical properties.

For example, the Mycoplanecin in the mycelial portion can be extracted by the addition of a water-miscible solvent, such as methanol, ethanol, isopropanol or acetone. The solvent is then removed from the extract and the residue is re-extracted with a water-immiscible solvent, such as chloroform, ethyl acetate, methyl isobutyl ketone or methylene chloride. The Mycoplanecin contained in the liquid portion of the culture broth can also be extracted with such a water-immiscible solvent, after which it would normally be combined with the extract from the mycelial portion and concentrated to give a crude Mycoplanecin extract.

Alternatively, Mycoplanecin can be extracted by adding a water-miscible solvent, such as those exemplified above, directly to the culture broth without separating the mycelium from the liquid portion; the resulting extract is filtered and concentrated to remove the solvent and then the residue is re-extracted, as in the procedure described above, with a water-immiscible solvent.

The Mycoplanecin thus obtained may be further purified by any of the methods well-known for the purification of compounds having similar physico-chemical properties; however, we prefer to use purification techniques employing an adsorbent or a counter-current distribution method. Suitable adsorbents include alumina, silica gel, Sephadex (a Trade Mark for a range of polysaccharide-derived organic compounds) or cellulose. We particularly prefer a column chromatography separation method employing silica gel as carrier and methanol, ethyl acetate or chloroform or any mixture thereof as eluent. Preparative thin layer chromatography employing silica gel is also effective for producing more highly purified Mycoplanecin.

The purified Mycoplanecin thus obtained shows single spots in coloration reactions with sulphuric acid, potassium permanganate or iodine on a silica gel thin layer chromatogram and also has the physical and chemical properties heretofor described.

The minimal inhibitory concentrations (MIC) of Mycoplanecin against various microorganisms is shown in Table 6. The evaluation was made as follows: for mycobacteria, after incubation for 5 weeks at 37° C. by a dilution method employing a 1% bovine serum-containing Dubos liquid medium; on general bacteria, after incubation for 24 hours at 37° C. by an agar dilution method, employing a heart infusion agar medium; and on fungi and yeasts, after incubation for 48 hours at 26° C. by an agar dilution method employing Sabouraud's agar medium.

TABLE 6

| Test organism | Medium* | MIC (μg/ml) |
| --- | --- | --- |
| *Mycobacterium kansasii* IFM 2069 | DM | 0.025 |
| *Mycobacterium fortuitum* IFM 2079 | DM | 1.56 |
| *Mycobacterium intracellulare* IFM 2073 | DM | 0.39 |
| *Mycobacterium intracellulare* IFM 2083 | DM | 0.39 |
| *Mycobacterium tuberculosis* IFM 2026 Matsudo | DM | 0.195 |
| *Mycobacterium tuberculosis* IFM 2027 Maru | DM | 0.39 |
| *Mycobacterium tuberculosis* IFM 2028 $H_{37}$ | DM | 0.78 |
| *Mycobacterium tuberculosis* IFM 2029 $H_{37}Rv$ | DM | 0.39 |
| *Mycobacterium tuberculosis* IFM 2030 $H_2$ | DM | 0.78 |
| *Mycobacterium bovis* BCG IFM 2031 | DM | 0.78 |
| *Mycobacterium bovis* ushi-10 IFM 2032 | DM | 0.1 |
| *Mycobacterium tuberculosis* (Streptomycin-resistant) IFM 2033 | DM | 0.1 |
| *Mycobacterium smegmatis* ATCC 607 | DM | 0.08 |
| *Mycobacterium phlei* | DM | 0.01 |
| *Micrococcus luteus* PCI 1001 | H | 0.0125 |
| *Staphylococcus aureus* 209P JC-1 | H | >400 |
| *Bacillus subtilis* PCI 219 | H | >400 |
| *Escherichia coli* NIHJ JC-2 | H | >400 |
| *Klebsiella pneumoniae* PCI 602 | H | >400 |
| *Proteus vulgaris* OX 19 | H | >400 |
| *Proteus mirabilis* 1331 | H | >400 |
| *Pseudomonas aeruginosa* SANK 73860 | H | >400 |
| *Candida albicans* Yu 1200 | S | >400 |
| *Aspergillus oryzae* SANK 11262 | S | >400 |
| *Penicillium chrysogenum* SANK 12768 | S | >400 |
| *Trichophyton mentagrophytes* SANK 22374 | S | >400 |
| *Pyricularia oryzae* SANK 16975 | S | >400 |

*Medium DM: Dubos medium, except that 10% of bovine serum was added other than for the two strains *Mycobacterium smegmatis* ATCC 607 and *Mycobacterium phlei*.
Medium H: Heart infusion agar medium.
Medium S: Sabouraud's agar medium.

The toxicity of the antibiotic substance, Mycoplanecin, was investigated by administering it intraperitoneally to mice at a dose of 100 mg/kg body weight; no mice died.

The preparation of Mycoplanecin is illustrated by the following non-limiting Examples.

EXAMPLE 1

To a 500 ml Sakaguchi flask were added 100 ml of a seed culture medium having a pH of 7.0 before sterilization and the following composition (percentages are w/v):

| | | |
|---|---|---|
| Glucose | 1% | |
| Glycerine | 1% | |
| Oatmeal | 0.5% | |
| Sucrose | 1% | |
| Soybean meal | 2% | |
| Casamino acid | 0.5% | |
| Live yeast | 1% | |
| Calcium carbonate | 0.1% | |
| Water q.s. | | |

This medium was inoculated with a culture of *Actinoplanes nov.* sp. Strain No. 41042 and reciprocal shaking culture was carried out at 28° C. for 96 hours. The resulting culture broth was divided into 5 ml portions and each portion was inoculated into a Sakaguchi flask each flask containing 100 ml of a production medium having a pH of 7.0 before sterilization and having the following composition (percentages are w/v):

| | | |
|---|---|---|
| Glycerine | 0.5% | |
| Sucrose | 2% | |
| Soybean meal | 1% | |
| Live yeast | 1% | |
| Corn steep liquor | 0.5% | |
| COCl$_2$ . 6H$_2$O | 0.001% | |
| Water q.s. | | |

Reciprocal shaking culture was then carried out at 28° C. for 96 hours. The resulting culture broths were combined.

To 4 liters of the combined culture broths (pH 7.2) were added 5% w/v of Celite 545 (a Trade Mark for a filter aid available from Johns Manville Product Corporation, U.S.A) and the broth was filtered to separate the liquor from the mycelia-containing filter cake. The filtrate was extracted with 2 liters of ethyl acetate to recover its Mycoplanecin content, whilst the mycelial cake was extracted with 2 liters of acetone containing 20% v/v water; the acetone was distilled off under reduced pressure and the residue was extracted with 2 liters of ethyl acetate. The ethyl acetate extracts from the filtrate and the mycelial cake were combined, to give 4 liters of combined extracts.

These combined extracts were washed twice, each time with 1 liter of a saturated aqueous solution of sodium chloride. The washed extracts were dehydrated over anhydrous sodium sulphate and then concentrated by evaporation under reduced pressure to give 1.07 g of an oily substance.

This oily substance was dissolved in a small volume of chloroform and adsorbed on a column containing 20 g of silica gel which had previously been prepared with chloroform. The column was then washed with chloroform and impurities were eluted away using a 1:1 by volume mixture of chloroform and ethyl acetate and then ethyl acetate alone. The desired Mycoplanecin was then eluted with a mixed solvent containing 95% by volume ethyl acetate and 5% by volume methanol. One liter of an active fraction was separated from the eluted fractions and concentrated by evaporation under reduced pressure to give 130 mg of a white powder.

110 mg of this white powder were dissolved in a small volume of chloroform and the resulting solution was passed into a 200 ml column containing Sephadex LH-20 (available from Pharmacia Co. Limited, Sweden) packed with chloroform, and which was then eluted with chloroform. Active fractions thus collected were concentrated by evaporation under reduced pressure to give 90 mg of Mycoplanecin as a white powder. This purified product showed single spots with iodine, sulphuric acid and potassium permanganate on a silica gel thin layer chromatograph.

EXAMPLE 2

Ten 500 ml Sakaguchi flasks, each containing 100 ml of a seed culture medium having the same composition as that described in Example 1, were inoculated with a culture of *Actinoplanes nov.* sp. Strain No. 41042, and reciprocal shaking culture was conducted at 28° C. for 96 hours.

A 30 liter jar fermenter, which contained 15 liters of a production medium having the same composition as that described in Example 1, was inoculated with 750 ml of the culture broth produced as described above and then this was subjected to shaking culture with agitation and aeration at 250 rpm, a temperature of 28° C. and an aeration of 15 liters/minute for 80 hours.

To the resulting culture broth were added 15 liters of acetone, the mixture was stirred and the product was filtered with the aid of 500 g of Celite. 25 liters of the filtrate were concentrated by evaporation under reduced pressure to distill off the acetone. To the residual liquid (15 liters) were added 7 liters of methylene chloride and extraction was carried out with shaking and agitation. The residue was further extracted with another 7 liters of methylene chloride and the extracts were combined, after which the solvent was evaporated off to give 1.8 g of an oily substance.

A solution of this oily substance in a small volume of chloroform was adsorbed on a column containing 50 g of silica gel and packed with chloroform, from which Mycoplanecin was eluted with a solvent system comprising 99% by volume chloroform and 1% by volume methanol.

400 ml of active fraction were collected and concentrated by evaporation under reduced pressure to give 390 mg of a white powder. A solution of this white powder in a small volume of chloroform was then subjected to preparative thin layer chromatography employing a silica gel plate (5717, available from Merck and Co. Inc.) developed with a 95:5 by volume mixture of chloroform and methanol. The active bands were extracted with ethyl acetate to give 250 mg of Mycoplanecin as a white powder having a purity of about 90% (by bioassay).

Figure 2:
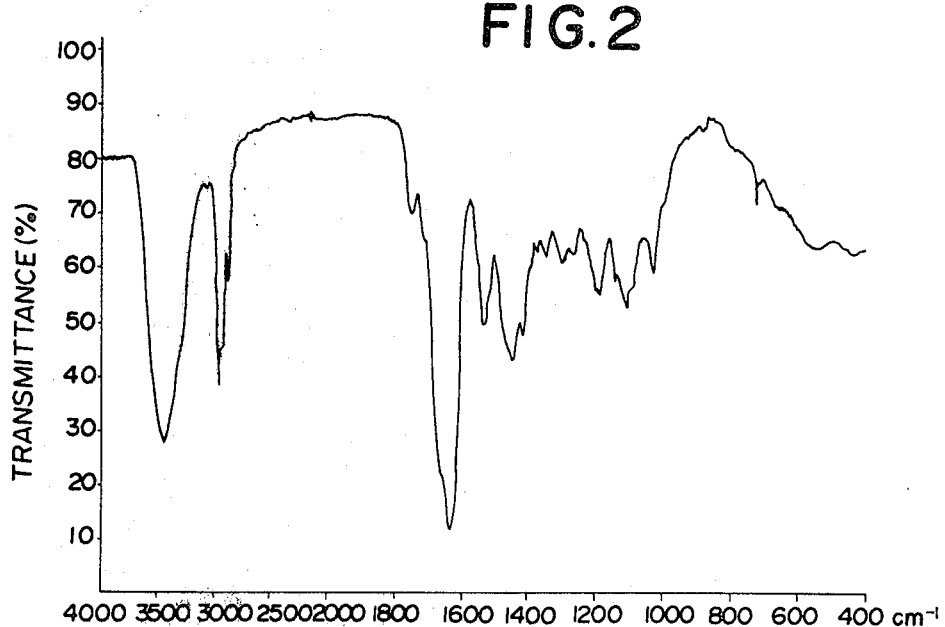
Figure 3:
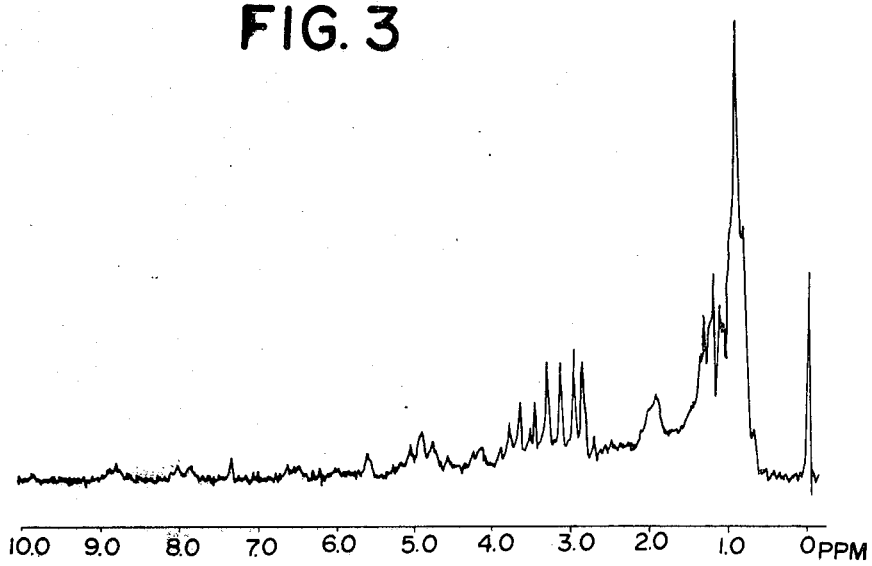

We claim:

1. An antibiotic substance, Mycoplanecin, characterized by the following properties:
   (1) Colour and state
       White powder;
   (2) Melting point
       161°–167° C.;
   (3) Specific rotation $[\alpha]^{21}_D$-66° (C=0.4, chloroform);
(4) Elemental analysis
C, 61.78%; H, 8.48%; N, 11.75%; (after drying to constant weight)
(5) Ultraviolet absorption spectrum
Only terminal absorption as shown in FIG. 1 of the accompanying drawings, when measured at 20 μg/ml in 50% v/v aqueous methanolic solution;
(6) Infrared absorption spectrum
The spectrum, measured in a KBr disc, is shown in FIG. 2 of the accompanying drawings;
(7) Nuclear magnetic resonance spectrum
The spectrum, as measured in deuterochloroform as solvent and with tetramethylsilane (TMS) as internal standard, is shown in FIG. 3 of the accompanying drawings;
(8) Solubility
Soluble in methanol, ethanol, ethyl acetate, acetone and chloroform;
sparingly soluble in benzene;
insoluble in water;
(9) Colour reaction
Brown-coloured with 50% v/v aqueous sulphuric acid; positive for iodine and potassium permanganate on silica gel thin layer chromatograms; negative for ninhydrin and 2,4-dinitrophenylhydrazine;
(10) Amino acid composition
1 mole each of glycine, proline, leucine, 2-amino-5-methylhexanoic acid, N-methylthreonine, N-methylleucine, methylproline and ethylproline, and 2 moles of N-methylvaline detected after hydrolysis with 6 N hydrochloric acid at 105° C. for 20 hours;
(11) Antibacterial activity
Strong antibacterial activity against various bacteria of the genus Mycobacterium.

2. A process for the production of an antibiotic substance, Mycoplanecin characterized by the following properties:
(1) Colour and state
White powder;
(2) Melting point
161°–167° C.;
(3) Specific rotation
$[\alpha]^{21}_D$-66° (C=0.4, chloroform);
(4) Elemental analysis
C, 61.78%; H, 8.48%; N, 11.75%; (after drying to constant weight)
(5) Ultraviolet absorption spectrum
Only terminal absorption as shown in FIG. 1 of the accompanying drawings, when measured at 20 μg/ml in 50% v/v aqueous methanolic solution;
(6) Infrared absorption spectrum
The spectrum, measured in KBr disc, is shown in FIG. 2 of the accompanying drawings;
(7) Nuclear magnetic resonance spectrum
The spectrum, as measured in deuterochloroform as solvent and with tetramethylsilane (TMS) as internal standard, is shown in FIG. 3 of the accompanying drawings;
(8) Solubility
Soluble in methanol, ethanol, ethyl acetate, acetone and chloroform;
sparingly soluble in benzene;
insoluble in water;
(9) Colour reaction
Brown-coloured with 50% v/v aqueous sulphuric acid; positive for iodine and potassium permanganate on silica gel thin layer chromatograms; negative for ninhydrin and 2,4-dinitrophenylhydrazine;
(10) Amino acid composition
1 mole each of glycine, proline, leucine, 2-amino-5-methylhexanoic acid, N-methylthreonine, N-methylleucine, methylproline and ethylproline; and 2 moles of N-methylvaline detected after hydrolysis with 6 N hydrochloric acid at 105° C. for 20 hours;
(11) Antibacterial activity
Strong antibacterial activity against various bacteria of the genus Mycobacterium;
which process comprises cultivating Actinoplanes nov. sp. Strain No. 41042, NRRL-11462 as the Mycoplanecin-producing microorganism in an aqueous nutrient medium containing an assimilatable carbon source and an assimilatable nitrogen source under aerobic conditions until substantial Mycoplanecin is imparted to said medium and isolating Mycoplanecin from said medium.

3. A process as claimed in claim 2, wherein said nutrient medium during cultivation is at a substantially neutral pH and at a temperature of from 18° to 30° C.

* * * * *